US00PP11382P

United States Patent [19]

Winchel

[11] Patent Number: Plant 11,382

[45] Date of Patent: May 16, 2000

[54] HYBRID TEA ROSE PLANT NAMED 'WEKWINWIN'

[75] Inventor: Joseph F. Winchel, Harbor City, Calif.

[73] Assignee: Weeks Wholesale Rose Grower, Inc., Upland, Calif.

[21] Appl. No.: 09/153,953

[22] Filed: Sep. 16, 1998

[51] Int. Cl.[7] ..... A01H 5/00

[52] U.S. Cl. ..... Plt./131

[58] Field of Search ..... Plt./130, 131, 132, Plt./142

*Primary Examiner*—Howard J. Locker

*Attorney, Agent, or Firm*—Christie, Parker & Hale, LLP

[57] ABSTRACT

A new variety of Hybrid Tea rose suitable for garden decoration, having flowers of bright red coloration with a reverse petal coloration of yellow.

1 Drawing Sheet

BACKGROUND OF THE INVENTION

This invention relates to a new and distinct variety of Hybrid Tea Rose. The varietal denomination of the new variety is 'WEKwinwin'. Its parentage is unknown because it was discovered as a seedling in a controlled planting of mixed rose varieties.

SUMMARY OF THE INVENTION

Among the features which distinguish the new variety from other presently available and known commercial rose cultivars are the following combination of characteristics: its golden yellow filaments with a base coloration of red orange, its distinct bicolor petal coloration of bright red on the inner petal surface and yellow on the outer petal surface, and its prickles of many sizes on all stages of growth. The plant is an upright growing plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'WEKwinwin' may be asexually propagated by cuttings, budding or grafting.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of August. Phenotypic expression may vary with environmental, cultural and climatic conditions, as well as differences in conditions of light and soil.

FLOWER

The new variety usually bears its flowers singly, sometimes in irregularly rounded clusters of two to three or more per stem on strong medium to long stems (about 46 to about 70 cms.). Outdoors, the plant blooms abundantly and nearly continuously during the growing season. The flowers have a slight tea fragrance.

BUD

The peduncle is about 7.5 to about 9.5 cms. in length, of average to heavy caliper, and usually stiff. It is almost entirely smooth, with very few stipitate glands and hairs. Peduncle color is between 144A and 146A.

Before the calyx breaks, the bud is about 1.7 to about 2 cms. in diameter at the widest point, about 2.4 to about 2.7 cms. in length, and pointed to ovoid in shape. The surface of the bud bears very few stipitate glands and some hairs, usually with slender mostly entire foliaceous parts extending beyond the tip of the bud to about ¼ or more of its length. Bud color is between 146B and 137C.

The inner surface of the sepals is covered with fine wooly tomentum; sepal margins are lined with some stipitate glands and hairs.

As the petals open (after the calyx breaks), the bud is about 2.2 to about 2.5 cms. in diameter at the widest point, about 3 to about 3.5 cms. in length, and very pointed to ovoid in form. The color of the under surfaces of the newly opened petals is between 8C and 11C. The color of the upper surfaces of the newly opened petals is between 46A and 45A. At the point where the petal attaches, there is a moderately large zone of between 6C and 9C in coloration.

BLOOM

When fully open, the bloom ranges from about 8.5 to about 11 cms. in diameter. Petalage is double with about 26 to 30 petals and about 1 to 4 petaloids arranged irregularly. When partially open, the bloom form is usually high centered, and the petals are moderately cupped to spiraled around the center with petal edges moderately rolled outward. When fully open, the bloom form is more cupped, and the petals are more loosely cupped to undulated with petal edges moderately rolled outward.

PETALS

The substance of the petals is moderately heavy and of medium thickness, with upper surfaces somewhat satiny to velvety and under surfaces somewhat shiny to satiny. The outer petals are nearly round to broadly obovate in shape with rounded apices. The inner petals are more broadly obovate in shape usually with rounded apices.

NEWLY OPENED FLOWER

The under surface of the outer, intermediate and inner petals is between 11C and 9D. The upper surface of the outer, intermediate and inner petals is between 47A and 46B. At the point where the petal attaches, there is a moderately large zone of between 6C and 9C in coloration.

The general tonality of the newly opened flower is between 47A and 46B with a distinct reverse coloration of between 11C and 9D.

THREE DAY OLD FLOWER

The under surface of the outer and inner petals is between 8D and 11D. The upper surface of the outer and inner petals is between 53C and 47A. At the point where the petal attaches, there is a moderately large zone of between 4C and 9D.

The general tonality of the three day old flower is between 53C and 47A with a distinct reverse coloration of between 4C and 9D.

On the spent bloom, the petals usually drop off cleanly.

In August in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average to many in number (approximately 125) and are arranged regularly about the pistils. The filaments are irregular in length, most with anthers. Filaments are near 9A in color, often suffused at the base with near 44B. The anthers are moderately small for the class and all open approximately at the same time. Anther color is near 9C when immature and near 166B at maturity. Pollen is somewhat sparse and near 11B in color.

FEMALE REPRODUCTIVE ORGANS

Pistils vary in number (approximately 80). The styles are somewhat uneven, average to long in length, moderately thin in caliper, and somewhat loosely bunched. Stigma color is near 11C. Style color is near 53B. Ovaries are usually all enclosed in the calyx.

Hips have not been observed on this variety when grown in Upland, Calif.

FOLIAGE

The compound leaves are usually comprised of three to five or more leaflets and are borne abundantly. The leaves are about 10.5 to about 15 cms. in length and about 8.5 to about 11.5 cms. in width at the widest point, moderately heavy in texture, and matte to semi-glossy in finish. The leaflets are about 4.5 to about 7 cms. in length and about 2.8 to about 4.5 cms. in width at the widest point, oval in shape with somewhat acute apices and moderately rounded bases. Their margins are usually serrate to slightly irregular.

The upper surface of the mature leaf is between 137A and 139A. The under surface of the mature leaf is between 138B and 191A. The upper surface of the young leaf is between 137B and 146B, sometimes suffused with between 183B and 178A. The under surface of the young leaf is between 144A and 146C, sometimes lightly suffused with between 178B and 183C.

The rachis is average in caliper and somewhat rough. The upper side is moderately grooved with few hairs and some stipitate glands on the edges of the grooves. The under side of the rachis is somewhat rough with some hairs and stipitate glands and about 2 to 3 or more very small prickles.

The stipules are about 1.7 to about 2.3 cms. in length with moderately narrow to medium width and medium length straight points that usually turn out at an angle of more than 45 degrees.

The plant displays an average degree of resistance to powdery mildew, blackspot and rust as compared to other commercial varieties grown under comparable conditions in Upland, Calif.

GROWTH

The plant has an upright to slightly spreading medium height growth habit (about 120 to about 140 cms. in height and about 90 to about 110 cms. spread at the widest point), with full branching. It displays moderately vigorous growth and the canes are of medium to heavy caliper for the class.

The color of the major stems is between 138B and 191A. They bear several large prickles which are about 0.8 to about 1.1 cms. in length. The large prickles are almost straight angled moderately downward with a moderately long narrow to medium width base; prickle color is between 165B and 164A. The major stem bears several moderate sized prickles of similar shape and coloration. There are several very small prickles of similar coloration. The small prickles are almost straight and do not angle downward.

The color of the branches is between 146B and 137A. They bear several large prickles which are of similar size and shape to the large prickles on the major stems; prickle color is between 160B and 162C. The branches bear several moderate sized prickles of similar shape and coloration. There are several very small prickles of similar coloration. The small prickles are almost straight but do not angle downward.

The color of the new shoots is between 144B and 143C sometimes suffused with between 183B and 178A. They bear several large prickles which are of similar size and shape to the large prickles on the major stems; prickle color is between 179B and 182A. The shoots bear several moderate sized prickles of similar shape and coloration. There are several very small prickles of similar coloration. The small prickles are almost straight but do not angle downward.

I claim:

1. A new and distinct rose plant of the variety substantially as described and illustrated herein.

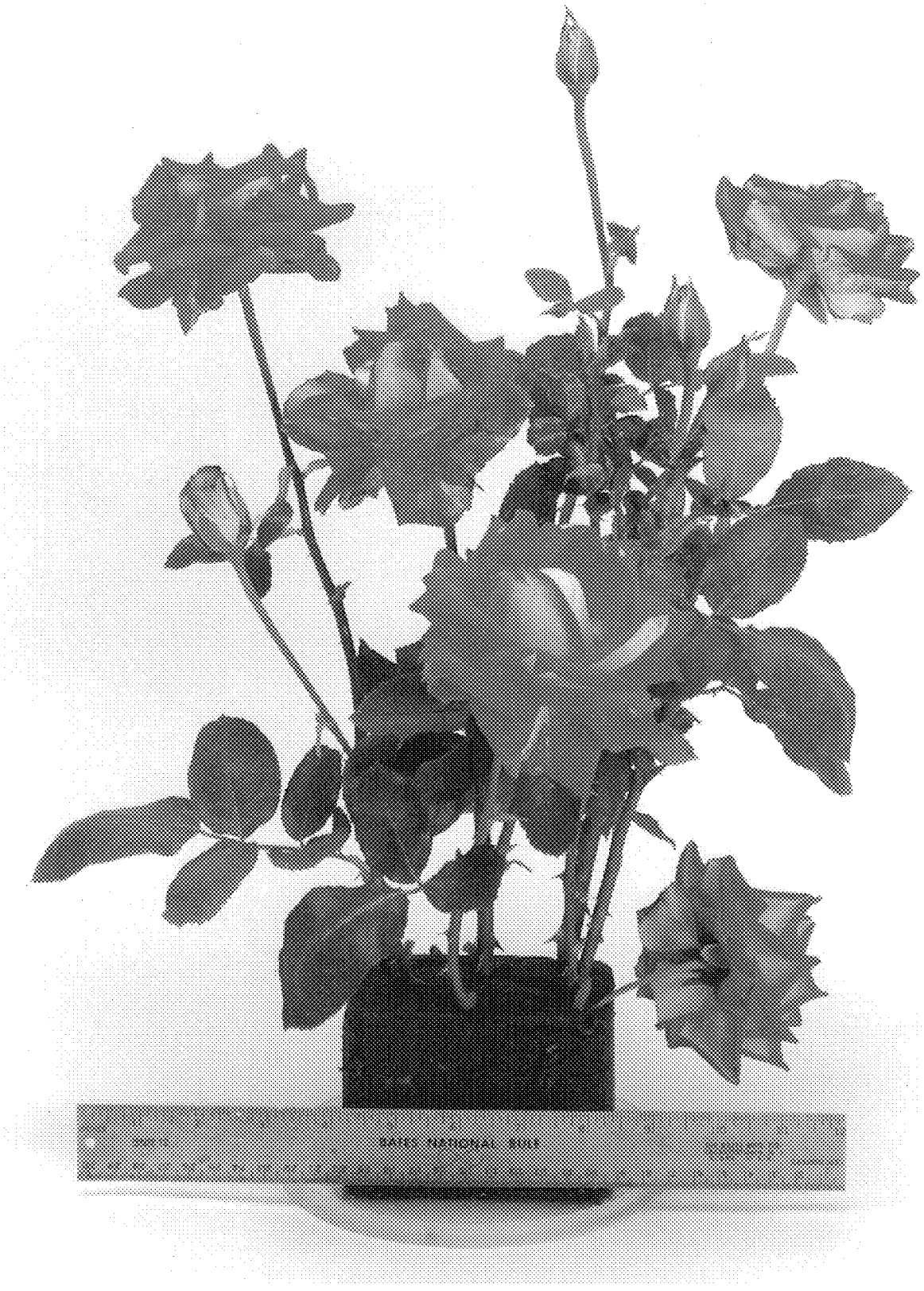

* * * * *